United States Patent
Goda et al.

(10) Patent No.: US 10,539,495 B2
(45) Date of Patent: Jan. 21, 2020

(54) SYSTEMS AND METHODS FOR GENERATING AN IMAGE OF AN INSPECTION OBJECT USING AN ATTENUATED BEAM

(71) Applicant: The University of Tokyo, Tokyo (JP)

(72) Inventors: Keisuke Goda, Tokyo (JP); Cheng Lei, Tokyo (JP)

(73) Assignee: THE UNIVERSITY OF TOKYO, Tokyo (JP)

(*) Notice: Subject to any disclaimer, the term of this patent is extended or adjusted under 35 U.S.C. 154(b) by 0 days.

(21) Appl. No.: 15/767,853

(22) PCT Filed: Oct. 14, 2016

(86) PCT No.: PCT/JP2016/080488
§ 371 (c)(1),
(2) Date: Apr. 12, 2018

(87) PCT Pub. No.: WO2017/065257
PCT Pub. Date: Apr. 20, 2017

(65) Prior Publication Data
US 2018/0299364 A1    Oct. 18, 2018

(30) Foreign Application Priority Data

Oct. 14, 2015  (JP) .................................. 2015-203231

(51) Int. Cl.
*G01N 15/14*  (2006.01)
*G01N 33/574*  (2006.01)
(Continued)

(52) U.S. Cl.
CPC .......... *G01N 15/14* (2013.01); *G01N 15/147* (2013.01); *G01N 15/1434* (2013.01);
(Continued)

(58) Field of Classification Search
None
See application file for complete search history.

(56) References Cited

U.S. PATENT DOCUMENTS

2004/0052484 A1* 3/2004 Broeng ............. C03B 37/01205
385/125
2008/0083255 A1   4/2008 Turner et al.
(Continued)

FOREIGN PATENT DOCUMENTS

| JP | 2011529230 A | 12/2011 |
| JP | 2013167582 A | 8/2013 |
| WO | 2014119660 A1 | 8/2014 |

OTHER PUBLICATIONS

Ugawa, M., et al., "High-throughput optofluidic particle profiling with morphological and chemical specificity," Optics Letters, vol. 40, No. 20, Oct. 15, 2015.
(Continued)

*Primary Examiner* — Michael P LaPage
(74) *Attorney, Agent, or Firm* — Fox Rothschild LLP; Robert J. Sacco; Carol E. Thorstad-Forsyth (57) ABSTRACT

According to the present invention, a probe beam (14) having undergone dispersive Fourier transformation by a dispersive Fourier transformation unit is spatially mapped, an inspection object (18, 20) is irradiated with the probe beam (14), and transmitted light (15) from the inspection object (18, 20) is detected, whereby an image is generated on the basis of the intensity of the transmitted light (15). Accordingly, an imaging apparatus can be provided which can irradiate the inspection object (18, 20) with the weak probe beam (14) having an intensity attenuated by the dispersive Fourier transformation unit, which can generate an image only by detecting the transmitted light (15) from the inspection object (18, 20), and which has a high throughput of generating images while an influence on the inspection object (18, 20) is suppressed.

7 Claims, 3 Drawing Sheets

(51) Int. Cl.
  *G01N 21/27* (2006.01)
  *G01N 15/10* (2006.01)
  *G02B 21/00* (2006.01)

(52) U.S. Cl.
  CPC ........... *G01N 21/27* (2013.01); *G01N 33/574* (2013.01); *G01N 2015/1006* (2013.01); *G01N 2015/144* (2013.01); *G01N 2015/1447* (2013.01); *G02B 21/002* (2013.01)

(56) References Cited

U.S. PATENT DOCUMENTS

| | | | |
|---|---|---|---|
| 2010/0314554 A1* | 12/2010 | Galimberti | G01J 3/02 250/458.1 |
| 2011/0168776 A1* | 7/2011 | Jalali | G06K 7/14 235/385 |
| 2013/0135529 A1* | 5/2013 | Jalali | G02B 21/002 348/571 |
| 2015/0056645 A1* | 2/2015 | Vacca | G01N 15/1459 435/29 |
| 2016/0223453 A1* | 8/2016 | Jalali | G01N 15/1434 |
| 2016/0231549 A1* | 8/2016 | Bosworth | G02B 21/008 |
| 2018/0286038 A1* | 10/2018 | Jalali | G06F 19/24 |

OTHER PUBLICATIONS

Lei, C., et al., "High-throughput label-free image cytometry and image-based classification of live Euglena gracilis," Biomedical Optics Express 2701, Jul. 1, 2016, vol. 7, No. 7, DOI:10.1364/BOE.7.002703.

\* cited by examiner

SYSTEMS AND METHODS FOR GENERATING AN IMAGE OF AN INSPECTION OBJECT USING AN ATTENUATED BEAM

CROSS-REFERENCE TO RELATED APPLICATIONS

The present application claims benefit of International Patent Application No. PCT/JP2016/080488, filed on Oct. 14, 2016, which claims the benefit and priority of Japanese Patent Application No. 2015-203231 filed on Oct. 14, 2015. The contents of the above applications are incorporated herein by reference in their entirety.

TECHNICAL FIELD

The present invention relates to an imaging apparatus, a flow cytometer, and an imaging method.

BACKGROUND ART

In the medical field, there has been a demand for cancer detection that can be performed easily in a short time by detection of whether or not a cancer cell is contained in collected blood. To this end, a trace amount of cancer cells needs to be detected, in a short time, from among a large amount of cells contained in blood.

Accordingly, a device for quickly, precisely, and low-invasively, at low cost, finding rare cells from among a population of an enormous number (e.g., one trillion or greater) of cells and analyzing the rare cells has been desired.

As a device for individually observing numerous cells, a flow cytometer has been conventionally known (see Patent Literature 1). Patent Literature 1 discloses a flow cytometer including a flow cell in which a sample liquid containing inspection objects flows as a laminar flow held at a prescribed flow rate, and including an imaging system which includes a high speed camera with a stroboscopic lamp and a burst CCD image sensor. In the flow cytometer disclosed in Patent Literature 1, inspection objects sequentially flowing in the flow cell in which the laminar flow has been formed are measured by means of the high speed camera, whereby the inspection objects are individually observed.

CITATION LIST

Patent Literature

Patent Literature 1: Japanese Patent Laid-Open No. 2013-167582

SUMMARY OF INVENTION

Technical Problem

However, in imaging with use of a conventional camera as in the flow cytometer disclosed in Patent Literature 1, when the flow rate of a sample liquid flowing in a flow cell is increased such that a large number of inspection objects are photographed in a short time, a blurred image is obtained due to an insufficient camera shutter speed.

Further, in imaging with use of a conventional camera, when the shutter speed is increased to enable higher speed imaging, an image having much noise is obtained due to insufficient sensitivity because the light reception amount of an imaging element is reduced.

Moreover, in imaging with use of a conventional camera, the light reception amount of an imaging element may be increased by application of auxiliary light such as strobe light, whereby the sensitivity will be enhanced. However, when the intensity of auxiliary light is increased, inspection objects may be destroyed. That is, an adverse influence may be exerted on the inspection objects.

As described above, since the shutter speed and the sensitivity of a conventional camera cannot be simultaneously satisfied and the speed for imaging inspection objects has a limit, the flow cytometer disclosed in Patent Literature 1 has a problem that the throughput of generating images cannot be increased without involving an influence on the inspection objects.

Therefore, an object of the present invention is to provide an imaging apparatus, a flow cytometer, and an imaging method, in which a high throughput of generating images is achieved while an influence on an inspection object is suppressed.

Solution to Problem

An imaging apparatus according to the present invention includes:

a probe beam generation unit configured to generate a probe beam;

a dispersive Fourier transformation unit configured to carry out dispersive Fourier transformation on the probe beam so as to map a spectrum of the probe beam in a time domain;

a spatial mapping unit configured to spatially map the probe beam having undergone the dispersive Fourier transformation and irradiate an inspection object with the probe beam;

a beam detection unit configured to detect transmitted light transmitted through the inspection object or scattered light scattered by the inspection object; and an image generation unit configured to generate an image of the inspection object in accordance with an intensity of the transmitted light or the scattered light.

The flow cytometer according to the present invention includes:

the imaging apparatus according to any one of claims 1 to 3; and a microfluidic device including a flow channel through which an inspection object can flow together with a fluid, wherein the imaging apparatus generates an image of the inspection object flowing through the flow channel.

An imaging method according to the present invention includes:

a probe beam generation step of generating a probe beam;

a dispersive Fourier transformation step of carrying out dispersive Fourier transformation on the probe beam so as to map a spectrum of the probe beam in a time domain;

a spatial mapping step of spatially mapping the probe beam having undergone the dispersive Fourier transformation and of irradiating an inspection object with the probe beam;

a beam detection step of detecting transmitted light transmitted through the inspection object or scattered light scattered by the inspection object; and an image generation step of generating an image of the inspection object in accordance with an intensity of the transmitted light or the scattered light.

Advantageous Effects of Invention

According to the present invention, the probe beam having undergone dispersive Fourier transformation by the dispersive Fourier transformation unit is spatially mapped, an inspection object is irradiated with the probe beam, and transmitted light or scattered light from the inspection object is detected, and an image is generated on the basis of the transmitted light or the scattered light. Therefore, an imaging apparatus, a flow cytometer, and an imaging method can be provided which can irradiate the inspection object with a weak probe beam having an intensity attenuated by the dispersive Fourier transformation unit, which can generate an image only by detection of the transmitted light or the scattered light from the inspection object, and which provide a high throughput of generating images while an influence on the inspection object is suppressed.

Figure 1:
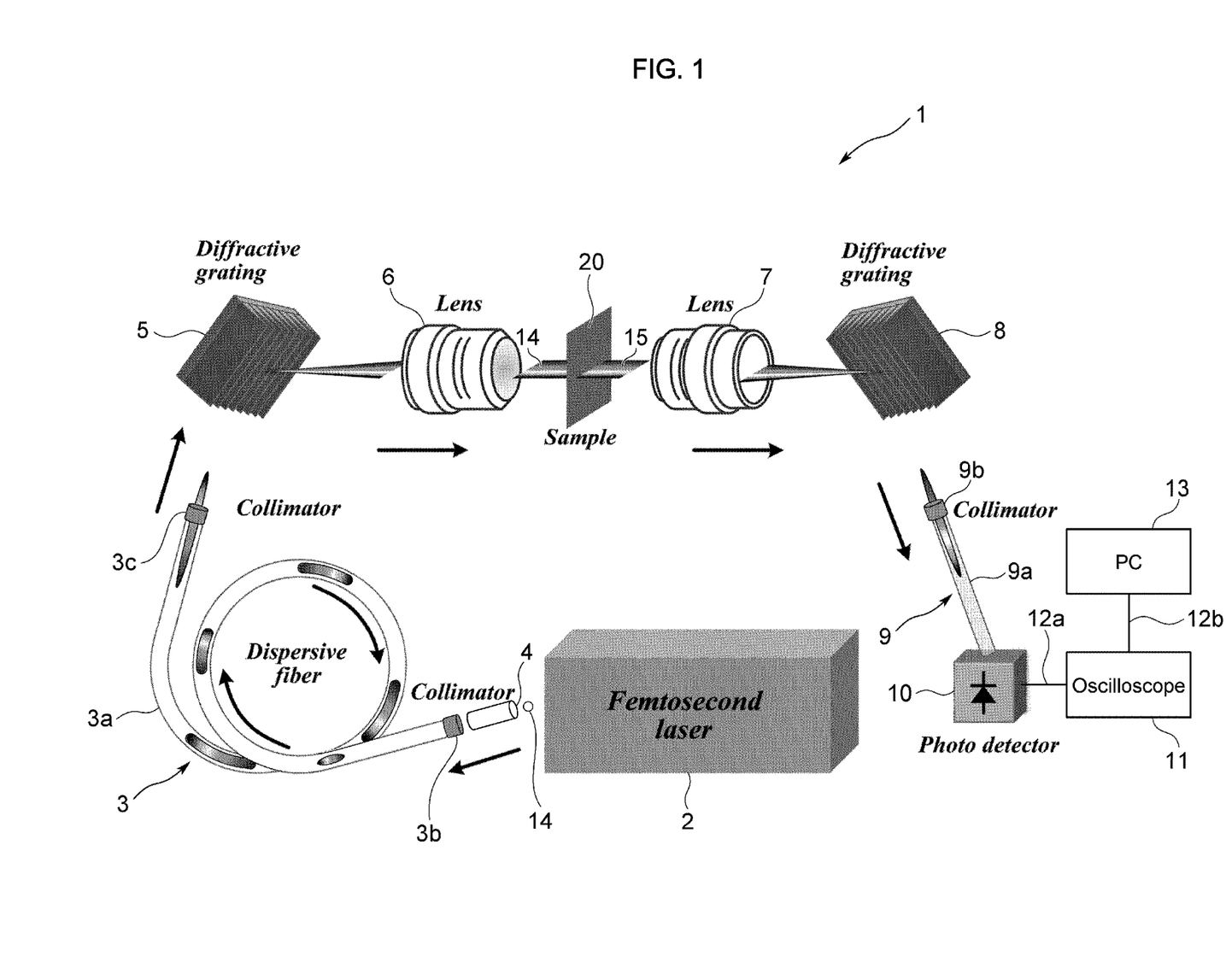
FIG. 1 is a schematic diagram illustrating the entire configuration of an imaging apparatus of an embodiment according to the present invention.

DESCRIPTION OF EMBODIMENTS (1) Imaging Apparatus According to Embodiment of the Present Invention (1-1) Configuration of Imaging Apparatus As illustrated in FIG. 1, an imaging apparatus 1 of the present embodiment includes an optical source 2, a dispersion element 4, a dispersive fiber 3, a first diffractive grating 5, a second diffractive grating 8, a first objective lens 6, a second objective lens 7, an introduction fiber 9, a photo detector 10, an oscilloscope 11, and a personal computer (PC) 13.

For example, the optical source 2 as a probe beam generation unit is a laser source such as a titanium-sapphire (Ti: $Al_2O_3$) femtosecond pulse laser (center wavelength: 790 nm, band width: 40 nm, repetition frequency: 75 MHz) which emits a wide-band pulse laser, and generates a probe beam 14 for generating an image of an inspection object 20 so as to probe the inspection object 20. The probe beam 14 is a wide-band optical pulse emitted from the optical source 2 with a predetermined repetition frequency.

In place of the aforementioned laser source, a laser source that is commonly used for optical communication and that emits a pulse laser may be used as the optical source 2. A laser source that emits a pulse laser having a center wavelength of 720 to 1600 nm can be used as the optical source 2.

The probe beam 14 generated by the optical source 2 enters the dispersion element 4 serving as a pre-dispersion unit. The dispersion element 4 is formed from glass, etc., and causes group velocity dispersion of light transmitted therethrough.

In the process of transmission of the probe beam 14, group velocity dispersion of the probe beam 14 is caused at the dispersion element 4 so that the velocities of wavelength components included in the probe beam 14 are changed according to the wavelengths. Accordingly, the time taken for transmission through the dispersion element 4 vary among the wavelength components, and, when the probe beam 14 exits from the dispersion element 4, a delay depending on the length of the wavelength occurs in the phase of each wavelength component. As a result, when exiting from the dispersion element 4, the probe beam 14 has a stretched pulse width as a result of change in the overlapping state of the wavelength components included in the probe beam 14, compared to when entering the dispersion element 4. In this way, the dispersion element 4 stretches out the waveform of the probe beam 14.

In the case of the present embodiment, the dispersion element 4 is formed into a rod-like shape having a length of 10 cm and a diameter of 0.5 cm, and is arranged so as to allow the probe beam 14 to be transmitted in the longitudinal direction thereof.

The imaging apparatus 1 of the present embodiment has the dispersion element 4 arranged therein, so that occurrence of an unfavorable nonlinear optical effect is suppressed at the dispersive fiber 3, which is described later, dispersive Fourier transformation on the probe beam 14 can be more reliably carried out, and an image of the inspection object 20 can be more clearly taken.

Note that the shape of the dispersion element 4 is not limited to a particular shape, and may be a rectangular parallelepiped shape or a polygonal pillar shape other than the aforementioned rod-like shape. Also, the diameter of the dispersion element 4 only needs to be sufficiently larger than a spot of the probe beam 14. The length of the dispersion element 4 can be selected, as appropriate, according to a desired pulse width to which the probe beam 14 is to be stretched out. As the length, a length of 10 to 50 cm is particularly preferable. When the length of dispersion element 4 is 10 to 50 cm, occurrence of a nonlinear effect at the dispersive fiber 3, which may have an adverse influence on dispersive Fourier transformation, can be sufficiently suppressed, which is described later.

The probe beam 14 transmitted through the dispersion element 4 enters the dispersive fiber 3 as a dispersive Fourier transformation unit. The dispersive fiber 3 is composed of a fiber main body 3a, and collimators 3b, 3c disposed at both ends of the fiber main body 3a.

The collimator 3b collimates the probe beam 14 having entered the collimator 3b, and causes the probe beam 14 converted into a collimated light (parallel light) to enter the fiber main body 3a.

The fiber main body 3a is formed of a single-mode optical fiber. In the fiber main body 3a, since the propagation speed of light through the fiber main body 3a varies according to the wavelength, group velocity dispersion of the probe beam 14 occurs in the process of transmission of the probe beam 14 and a velocity difference occurs among the wavelength components of the probe beam 14. As a result, when the probe beam 14 is transmitted through the fiber main body 3a, the pulse width of the probe beam 14 is stretched out as in the dispersion element 4.

When the probe beam 14 is propagated further through the fiber main body 3a after entering one end of the fiber main body 3a, the difference in a delay time among the wavelength components thereof becomes larger so that the pulse width is stretched out. When the probe beam 14 exits from the other end of the fiber main body 3a, the wavelength components thereof are separated from one another on the time axis. Thus, the pulse form of the probe beam 14 becomes a form similar to a spectrum form of the probe beam 14 as if the probe beam 14 underwent Fourier transformation on the time axis.

As described above, dispersive Fourier transformation is carried out on the probe beam 14 and the wavelength components of the probe beam 14 transmitted through the fiber main body 3a are mapped in a time domain. The pulse intensity of the probe beam 14 having undergone dispersive Fourier transformation represents the intensity of light having the corresponding frequency component. By adjustment of the length of the fiber main body 3a, the stretch of the pulse, that is, the time domain where the spectrum of the probe beam 14 is mapped can be adjusted, as appropriate.

In the case of the present embodiment, 630-HP (group velocity dispersion: 120 ps/nm/km, core diameter: 3.5 μm) manufactured by Nufern is used as the fiber main body 3a and the length thereof is set to 2 km. Thus, the spectrum of the probe beam 14 having exited from the other end of the fiber main body 3a is mapped in a time domain of 8 ns.

Note that the spectrum of the probe beam 14 is preferably mapped in a time domain from equal to or longer than 5 ns to shorter than the pulse period of the probe beam 14, and the length of the fiber main body 3a is preferably determined such that the spectrum of the probe beam 14 is mapped in a time domain from equal to or longer than 10 ns to shorter than the pulse period. Accordingly, imaging can be performed with high sensitivity.

The core diameter of the fiber main body 3a is not limited to a particular diameter, but is desirably 3 to 4 μm. By use of an optical fiber having a core diameter of 3 to 4 μm as the fiber main body 3a, mode dispersion of the probe beam 14 is sufficiently induced even when a pulse laser having a center wavelength around 800 nm (more specifically, a center wavelength of 750 to 850 nm) is used as the probe beam 14. Thus, dispersive Fourier transformation can be carried out on the probe beam 14. Also, by use of the pulse laser having a center wavelength around 800 nm, the spatial resolution can be enhanced.

Since a pulse laser having a center wavelength around 800 nm does not include a wavelength that is easily absorbed by water, the pulse laser is less likely to be influenced by moisture during imaging. Such a pulse laser is effective particularly in a case where the inspection object 20 that contains moisture, such as a cell, is to be imaged, or the inspection object 20 flowing in water is to be imaged in flow cytometry.

The collimator 3c collimates the probe beam 14 having undergone dispersive Fourier transformation and entered the collimator 3c, and causes the resultant collimated probe beam 14 to exit therefrom. As the collimators 3b, 3c, known collimators can be used, as appropriate, so as to be suitable for the fiber main body 3a.

As described above, the dispersive fiber 3 carries out dispersive Fourier transformation on the probe beam 14 and maps the spectrum of the probe beam 14 in the time domain.

Further, the probe beam 14 is attenuated in the process of being transmitted through the dispersive fiber 3 so that the peak intensity thereof is lowered. The imaging apparatus 1 irradiates the inspection object 20 with the probe beam 14 the peak intensity of which has been lowered. Therefore, an influence of imaging can be suppressed from being exerted on the inspection object 20.

For example, in a case where the inspection object 20 is an algal cell or the like, when the algal cell is irradiated with the probe beam 14 having not been transmitted through the dispersive fiber 3, the algal cell is highly likely to die or be greatly damaged because the probe beam 14 is a light pulse from a pulse laser and has a high peak intensity.

On the other hand, in the imaging apparatus 1, the probe beam 14 is attenuated by being transmitted through the dispersive fiber 3 and the algal cell is irradiated with the probe beam 14 the peak intensity of which has been lowered. Therefore, the influence of imaging can be suppressed from exerting on the algal cell and an image of the algal cell in a living condition can be generated.

The probe beam 14 having undergone dispersive Fourier transformation and exited from the other end of the dispersive fiber 3 strikes on the first diffractive grating 5 as a spatial mapping unit. The first diffractive grating 5 diffracts and spatially disperses the probe beam 14 that has struck thereon, and irradiates the inspection object 20 with the dispersed probe beam 14.

Since the diffraction angle of the probe beam 14 having struck on the first diffractive grating 5 varies depending on the wavelength component, a beam spatially spread in a 1D field is obtained. The wavelength components of the beam are spatially mapped (undergone Fourier transformation).

When the inspection object 20 is irradiated with the resultant probe beam 14, the region (hereinafter, referred to as a spot) in a surface of the inspection object 20 on which the probe beam 14 has struck has a linear shape. Since the wavelength components of the probe beam 14 are spatially mapped, the wavelength of the beam varies depending on the position in the spot on which the beam strikes.

Accordingly, the wavelength components included in the probe beam 14 can be associated with the positions on which the probe beam 14 strikes (at which the probe beam 14 is transmitted) so that the positions at which the probe beam 14 is transmitted through the inspection object 20 can be labeled on the basis of the wavelength.

In the case of the present embodiment, the first diffractive grating 5 is a planar diffractive grating having, in a surface thereof, grooves formed at a density of 1200 grooves/mm. A diffractive grating having a diffraction efficiency of 50 to 80% can be used as the first diffractive grating 5. Note that the diffractive gratings are used as spatial mapping units in the present embodiment but spectroscopic elements such as prisms may be used in place of the diffractive gratings.

The probe beam 14 disperse by the first diffractive grating 5 is condensed by the first objective lens 6, and the inspection object 20 is irradiated with the condensed probe beam 14. The probe beam 14 applied on the inspection object 20 is scattered and diffracted in the process of being transmitted through the inspection object 20, and the intensity thereof varies depending on the structure, of the inspection object 20, at the transmitted position. Thus, transmitted light 15 transmitted through the inspection object 20 includes information about the inspection object 20 as the intensity of the transmitted light 15.

Since the position at which the probe beam 14 is transmitted is labeled on the basis of the wavelength, the transmitted light 15 is detected and the intensities of the wavelength components thereof are acquired, whereby a 1D image of the inspection object 20 can be generated.

In the case of the present embodiment, the inspection object 20 is not limited to a particular object as long as the probe beam 14 can be transmitted through the object. The inspection object 20 may be a cell or an alga. In FIG. 1, the inspection object 20 is illustrated as a planar object for convenience. The inspection object 20 is arranged at the focal position of the first objective lens 6.

The transmitted light 15 transmitted through the inspection object 20 is transmitted through the second objective lens 7, is condensed, and strikes on the second diffractive grating 8. The second objective lens 7 is an objective lens identical to the first objective lens, and is arranged so as to have a focal point position that agrees with the focal position of the first objective lens 6. In the case of the present embodiment, objective lenses (manufactured by Olympus) with a magnification of 40× and a numerical aperture of 0.6 are used for the first objective lens 6 and the second objective lens 7. However, lenses can be selected, as appropriate, as the first objective lens 6 and the second objective lens 7 such that the spot size can be changed according to the size of the inspection object 20.

The second diffractive grating 8 diffracts and combines the transmitted light 15 having struck thereon, and converts the transmitted light 15 into an optical pulse. In the case of the present embodiment, a diffractive grating identical to the first diffractive grating 5 is used as the second diffractive grating 8. The wavelength components of the combined transmitted light 15 are mapped in a time domain, similar to those of the probe beam 14.

The transmitted light 15 converted into the optical pulse by the second diffractive grating 8 is introduced to the photo detector 10 as a beam detection unit through the introduction fiber 9. The introduction fiber 9 is formed of a fiber main body 9a and a collimator 9b. The collimator 9b is attached to one end of the fiber main body 9a, and the photo detector 10 is connected to the other end of the fiber main body 9a.

A common optical fiber may be used as the fiber main body 9a, and the collimator 9b may be selected, as appropriate, so as to be suited for the fiber main body 9a.

The photo detector 10 detects, before a next light pulse arrives, the transmitted light 15 converted into an optical pulse and converts the optical pulse into an electric signal pulse. In the case of the present embodiment, New Focus 1580-B (detection bandwidth: 12 GHz) manufactured by Newport is used as the photo detector 10. However, another photo detector may be used as the photo detector 10 as long as the photo detector can detect the pulse of the transmitted light 15 and convert the pulse into an electric signal.

The electric signal pulse of the transmitted light 15 generated by the photo detector 10 is sent to the oscilloscope 11 as a digitizer, which is connected to the photo detector 10 via a line 12a, and is converted into electronic data for each pulse. The oscilloscope 11 detects the electric signal pulse with a detected bandwidth of 16 GHz and a sampling frequency of 12.5 GS/s. The electronic data includes the time and the intensity of the electric signal pulse. In the case of the present embodiment, DPO71604B manufactured by Tektronix is used as the oscilloscope 11. However, the oscilloscope 11 is not limited to a particular oscilloscope as long as the oscilloscope 11 can sequentially digitize pulse signals.

The electronic data of the transmitted light 15 generated by the oscilloscope 11 is sent to the PC 13, which is connected to the oscilloscope 11 via a line 12b, and is stored in a storage device (not illustrated in FIG. 1) of the PC 13.

The PC 13 as an image generation unit executes, at a calculation unit (not illustrated in FIG. 1) of the PC 13 composed of a processor, etc., an image processing program stored in the storage device of the PC 13, and generates a 1D image of the inspection object 20 on the basis of the electronic data about the transmitted light 15 stored in the storage device of the PC 13. The generated 1D image is stored as 1D image data in the storage device of the PC 13.

The pulse intensity of the transmitted light 15 includes information about the inspection object 20 at a position at which the transmitted light 15 has been transmitted. The position at which the transmitted light 15 has been transmitted through the inspection object 20 corresponds to a wavelength component of the transmitted light 15. Moreover, the wavelength component of the transmitted light 15 (the probe beam 14) is mapped in a time domain and corresponds to the time of the detected pulsed light, and thus, the position at which the transmitted light 15 has been transmitted through the inspection object 20 corresponds to the time. Accordingly, an image of the inspection object 20 can be generated from the electronic data of the time and the pulse intensity stored in the storage device of the PC 13. The 1D image is generated on the basis of the pulse intensity of the transmitted light 15 such that the magnitude of the pulse intensity of the transmitted light 15 is expressed as an image gradation.

Furthermore, by the image processing program, data of multiple 1D images which are obtained by imaging the inspection object 20 at different positions is processed and the multiple 1D images are combined, so that a 2D image of the inspection object 20 can be generated.

The data of multiple 1D images to be used for combining is obtained by, for example, a method of continuously generating 1D images while moving the inspection object 20 in a direction orthogonal to the linear spot of the probe beam 14 and of storing the 1D images as image data. A generated 2D image is also stored as 2D image data in the storage device of the PC 13. The respective numbers of pixels in 1D images or a 2D image to be generated can be set, as appropriate.

As described above, the imaging apparatus 1 can image the inspection object 20 and generate images (1D images and a 2D image) of the inspection object 20.

(1-2) Operation and Effects

In the aforementioned configuration, the imaging apparatus 1 according to the present invention is configured to include the probe beam generation unit (optical source 2) configured to generate the probe beam 14 which is an optical pulse by emitting a pulse laser, the dispersive Fourier transformation unit (dispersive fiber 3) configured to carry out dispersive Fourier transformation on the probe beam 14 so as to map a spectrum of the probe beam 14 in a time domain, the spatial mapping unit (first diffractive grating 5) configured to spatially map the probe beam 14 having undergone dispersive Fourier transformation, and irradiate the inspection object 20 with the mapped probe beam 14 through the first objective lens 6, the beam detection unit (photo detector 10) configured to detect the transmitted light 15 transmitted through the inspection object 20, and the image generation unit (PC 13) configured to generate an image of the inspection object 20 in accordance with the pulse intensity of the transmitted light 15.

The imaging apparatus 1 according to the present invention is configured to generate the probe beam 14 which is an optical pulse by means of the optical source 2 (a probe beam generation step), carry out dispersive Fourier transformation on the probe beam 14 so as to map a spectrum of the probe beam 14 by means of the dispersive fiber 3 (a dispersive Fourier transformation step), spatially map the probe beam 14 having undergone dispersive Fourier transformation and irradiate the inspection object 20 with the mapped probe beam 14 by means of the first diffractive grating 5 (a spatial mapping step), detect the transmitted light 15 transmitted through the inspection object 20 by means of the photo detector 10 (a beam detection step), and generate an image of the inspection object 20 in accordance with the transmitted light 15 (an image generation step).

Therefore, in the imaging apparatus 1, the probe beam 14 having undergone dispersive Fourier transformation is spatially mapped in the 1D field by the dispersive fiber 3, the inspection object 20 is irradiated with the resultant probe beam 14, the transmitted light 15 from the inspection object 20 is detected, and an image is generated in accordance with the transmitted light 15. Hence, an image can be generated only by detection of transmitted light from an inspection object, and the image can be generated with a high throughput.

In addition, in the imaging apparatus 1, the inspection object 20 is irradiated with the probe beam 14 having been transmitted through the dispersive fiber 3 and undergone dispersive Fourier transformation, so that the inspection object 20 can be irradiated with the probe beam 14 the intensity of which has been attenuated by the dispersive fiber 3. Thus, the influence of imaging on the inspection object 20 can be suppressed. A more detailed description thereof is given below. The intensity of a beam is attenuated after passing through the dispersive fiber 3. In a configuration in which the dispersive fiber 3 is arranged after the inspection object 20, the optical source 2 is required to emit laser light having a sufficient intensity in order to ensure a sufficient light intensity for detection by the photo detector 10. Accordingly, light having a high intensity is applied to the inspection object 20 before being attenuated. This may cause a problem that the inspection object 20 is damaged particularly in a case where the inspection object 20 is a living cell or the like. Here, when the dispersive fiber 3 is arranged before the inspection object 20, the inspection object 20 is irradiated with light the intensity of which has been attenuated. As a result, an advantageous effect of lessening a damage caused by the light to the inspection object 20 can be provided.

Also, in the configuration in which the dispersive fiber 3 is arranged before the inspection object 20, an advantageous effect of lessening difficulty in coupling can be provided. An angle at which light applied to the inspection object 20 is scattered varies according to a slight positional deviation of the inspection object 20. However, in some cases, the position of the inspection object 20 is difficult to set with high precision in a flow cytometer, etc. Meanwhile, a very thin fiber is generally expected to be used as the dispersive fiber 3. Thus, in a case where the dispersive fiber 3 is arranged after the inspection object 20, transmitted light from the inspection object 20 needs to be coupled to the dispersive fiber 3 with precision. There is a problem that such precise coupling is very difficult under the aforementioned condition in which the position of the inspection object 20 cannot be set with precision. In the configuration in which the dispersive fiber 3 is arranged before the inspection object 20, light emitted from the optical source 2 may be coupled to the dispersive fiber 3, variation of the accuracy of the coupling is smaller, compared to coupling of the transmitted light from the inspection object 20. Therefore, the position alignment becomes easy and the alignment can be easily held. Further, since the transmitted light from the inspection object 20 may be coupled to a thicker fiber or may be condensed directly on the photo detector 10, the accuracy required for the position alignment can be greatly eased. For this reason, in the configuration in which the dispersive fiber 3 is arranged before the inspection object 20, the accuracy required for optical alignment can be greatly eased, whereby an effect of enhancing the apparatus stability, etc. can be provided.

(2) Flow Cytometer According to Embodiment of the Present Invention

(2-1) Configuration of Flow Cytometer

Figure 2:
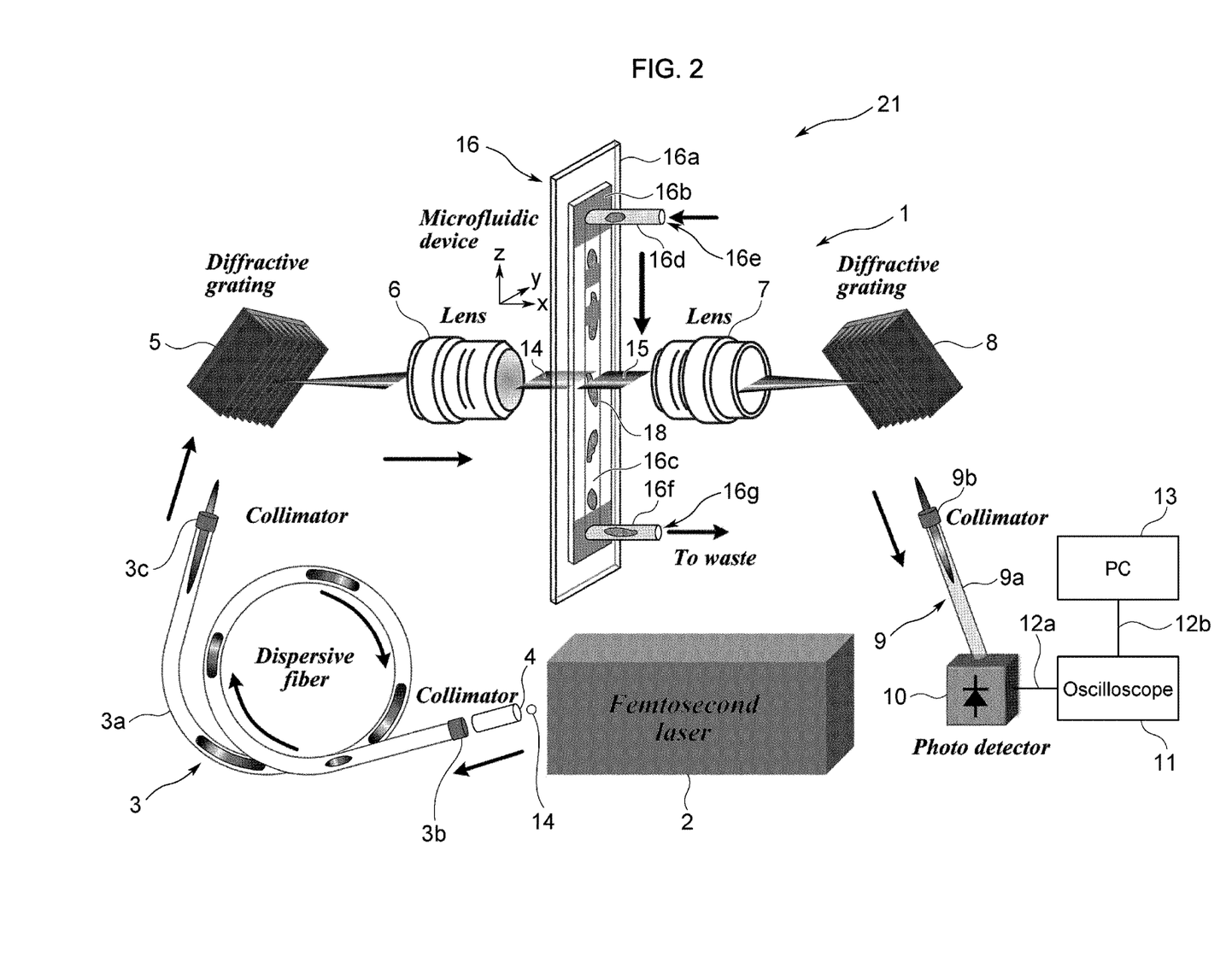
FIG. 2 is a schematic diagram illustrating the entire configuration of a flow cytometer of the embodiment according to the present invention.

As illustrated in FIG. 2 in which components identical to those in FIG. 1 are denoted by the same reference numerals, a flow cytometer 21 includes the imaging apparatus 1 of the present embodiment and a microfluidic device 16.

The microfluidic device 16 includes a base part 16a which is formed of a glass substrate, for example, and a main body 16b which is attached to a surface of the base part 16a and which is made from polydimethylsiloxane (PDMS), for example.

In one surface of the main body 16b, a groove 16c having a U-shaped cross section is formed. The groove 16c is formed into a linear shape extending in the longitudinal direction of the main body 16b. The groove 16c does not penetrate the main body 16b, has an end which is a terminal end of the groove 16c. In the end of the groove 16c, a through hole (not illustrated in FIG. 2) extending from the bottom of the groove 16c to a surface opposite to the surface having the groove 16c formed therein, is formed. The surface, of the main body 16b, in which the groove 16c is formed is attached to the base part 16a.

Accordingly, in the microfluidic device 16, a space surrounded by both side surfaces and the bottom surface of the groove 16c and by a surface of the base part 16a forms a flow channel through which an inspection object 18 can flow together with a fluid. In the microfluidic device 16, a fluid can be put into the flow channel through a though hole formed in the bottom at one end of the groove 16c, and the fluid can be discharged from the flow channel to the outside through a through hole formed at the bottom at one end of the groove 16c.

In the case of the present embodiment, a fluid introduction pipe 16d which is composed of PEEK (registered trademark) tubing manufactured by Upchurch Scientific, for example, is connected to the through hole in the one end of the groove 16c, and a fluid discharge pipe 16f which is formed of PEEK (registered trademark) tubing similar to the fluid introduction pipe 16d, is connected to the through hole in the other end of the groove 16c. As a result of provision of the fluid introduction pipe 16d, a fluid can be introduced through an opening 16e at one end of the fluid introduction pipe 16d. Thus, a fluid can be easily introduced into the flow channel in the microfluidic device 16. Also, as a result of provision of the fluid discharge pipe 16f, the fluid can be discharged from an opening 16g at one end of the fluid discharge pipe 16f. Thus, a fluid having passed through the flow channel in the microfluidic device 16 can be easily recovered.

In the case of the present embodiment, the groove 16c is produced so as to have a cross section formed into a rectangular shape of 80 μm (width)×70 μm (depth). However, the cross-section shape and the cross-section area are not limited to a particular shape and a particular area, and may be selected, as appropriate, so as to be suited for the size of the inspection object 18. The sizes and shapes of the through holes, the fluid introduction pipe 16d, the fluid discharge pipe 16f, the base part 16a, and the main body 16b may also be selected, as appropriate, so as to be suited for the size of the produced flow channel. In addition, materials of the base part 16a, the main body 16b, the fluid introduction pipe 16d, and the fluid discharge pipe 16f may be selected, as appropriate. The microfluidic device 16 is not limited to a particular microfluidic device as long as the microfluidic device can be transmitted the probe beam 14 therethrough and can allow the inspection object 18 to flow together with a fluid therethrough. As the microfluidic device 16, a commercially available microfluidic device or a flow cell can be used.

In the present embodiment, an alga as the inspection object 18 flows together with water in the flow channel in the microfluidic device 16.

In the flow cytometer 21, the microfluidic device 16 is arranged such that, when the propagation direction of the probe beam 14 (transmitted light 15) from the first objective lens 6 to the second objective lens 7 is defined as an X direction and a direction orthogonal to the X direction and in which the probe beam 14 is spatially spread in the 1D field is defined as a Y direction, the direction in which the inspection object 18 flows through the flow channel is parallel with a Z direction perpendicular to the X and Y directions, and the probe beam 14 is transmitted in the thickness direction of the microfluidic device 16. Also, the microfluidic device 16 is arranged such that the focal positions of the first objective lens 6 and the second objective lens 7 are located in the flow channel and the probe beam 14 is transmitted, at a point near the focal positions, through the inspection object 18.

In the flow cytometer 21, the imaging apparatus 1 generates an image of the inspection object 18 flowing through the flow channel in the microfluidic device 16 together with a fluid. Since the inspection object 18 flows through the flow channel in the microfluidic device 16, a position at which the probe beam 14 is transmitted through the inspection object 18 is gradually shifted, according to the flow rate of the fluid flowing through the flow channel, toward a direction opposite to the direction in which the inspection object 18 flows. Hence, the probe beam 14 is continuously generated by the optical source 2 of the imaging apparatus 1, 1D images of the inspection object 18 are continuously generated, and thus, 1D images taken at the photographing positions of the inspection object 18 shifted by the movement amount of the inspection object 18 during the cycle of the probe beam 14, can be sequentially generated.

In the flow cytometer 21, such 1D images of the inspection object 18 taken at the shifted photographing positions of the inspection object 18 are combined, whereby a 2D image of the inspection object 18 can be generated.

(2-2) Operation and Effects

In the aforementioned configuration, the flow cytometer 21 of the present embodiment is configured to include the imaging apparatus 1 and the microfluidic device 16 including the flow channel through which the inspection object 18 can flow together with a fluid, wherein the imaging apparatus 1 generates an image of the inspection object 18 flowing through the flow channel.

Therefore, the flow cytometer 21 generates an image of the inspection object 18 by means of the imaging apparatus 1 so that the influence on an inspection object can be suppressed during imaging and an image can be generated with a high throughput.

(3) Other Embodiments

In the aforementioned embodiment, the case has been described in which, in the imaging apparatus 1, the probe beam 14 is spatially mapped in the 1D field by the first diffractive grating 5 and 1D images are generated. However, the probe beam 14 mapped in the 1D field may be further disperse by use of a spectroscopic element or the like such that the probe beam 14 is spatially mapped in a 2D field, and the inspection object 18, 20 is irradiated with the resultant probe beam 14, whereby a 2D image can be generated.

Alternatively, the inspection object 18, 20 may be scanned with the probe beam 14 in a direction orthogonal to the linear spot of the probe beam 14, multiple 1D images may be generated at different points on the inspection object 18, 20, and the multiple 1D images are combined, whereby a 2D image can be also generated.

In the aforementioned embodiment, the transmitted light 15 is exclusively measured. However, scattered light may be measured. In this case, in order to prevent light transmitted through the inspection object 18, 20 from entering the second objective lens 7, an aperture or a slit is placed, as appropriate, before the second objective lens 7.

(4) Verification Test

With use of the flow cytometer 21 of the present embodiment, images of bead as the inspection objects 18 were generated.

In the verification test, a dispersion liquid obtained by dispersing, in water, beads each having a diameter of 10 μm and being formed from polystyrene was put into a syringe, and the dispersion liquid was introduced into the flow channel through the opening 16e of the fluid introduction pipe 16d with use of a syringe pump. Here, the syringe pump was set, as appropriate, so as to cause the dispersion liquid in the flow channel to flow at a flow rate of 1 m/s. A container (not illustrated) was placed under the opening 16g of the fluid discharge pipe 16f, the fluid and the beads discharged from the flow channel through the fluid discharge pipe 16f were stored in the container.

In the verification test, the beads flowing through the flow channel at the flow rate of 1 m/s were imaged by the imaging apparatus 1, and thus, images were generated. The images of the beads were generated by dividing the time domain of the optical pulse of the detected transmitted light 15 into 15 sections, continuously generating 700 data sets of 1D images (15 pixels) in a direction parallel with the Y direction in FIG. 2, and combining the 700 data sets of 1D images.

Figure 3A:
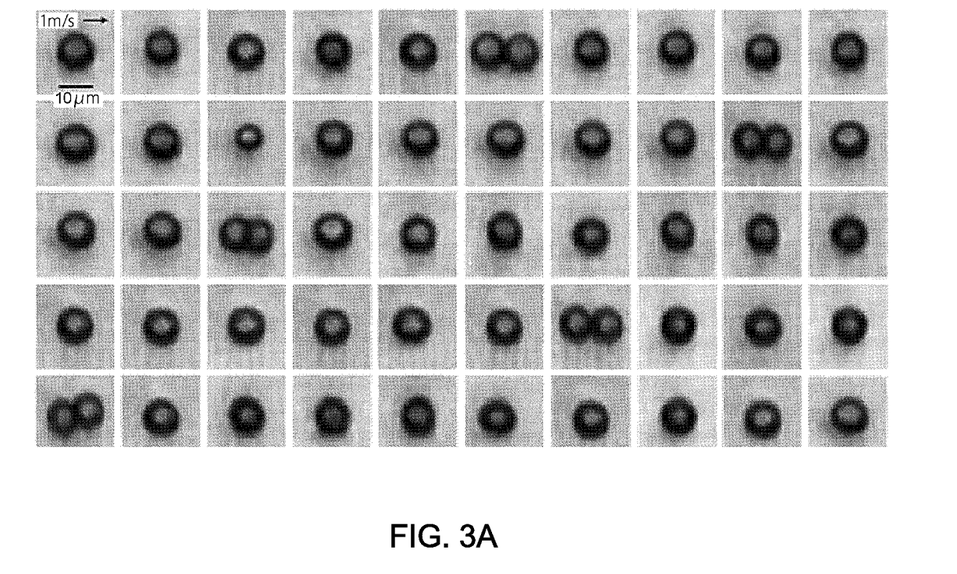
FIGS. 3A and 3B are images of beads flowing through a flow channel, which were generated by the imaging apparatus.
Figure 3B:
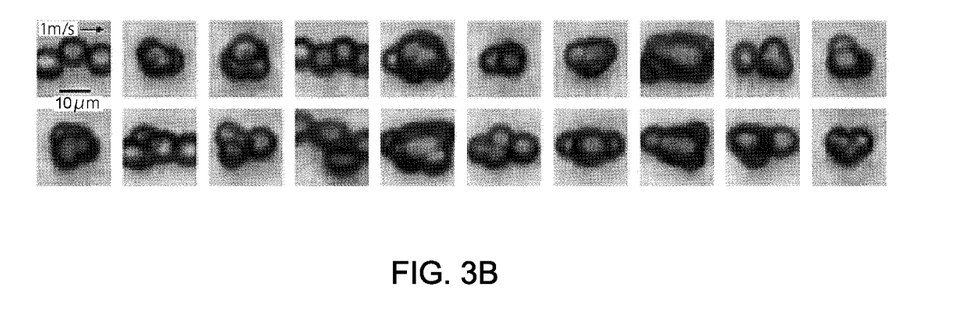

The generated images are shown in FIG. 3A and FIG. 3B. FIG. 3A shows that the imaging apparatus 1 succeeded in generating clear images of the beads flowing at 1 m/s. Further, FIG. 3B shows that even images in which multiple beads coupled to each other were identified were generated, and thus, the state of the beads can be correctly identified even in a condition in which beads are considered, by a conventional apparatus, to have large sized particles mixed therein due to an insufficient shutter speed or insufficient sensitivity.

Accordingly, the imaging apparatus 1 succeeded in imaging the inspection object 18 flowing at 1 m/s, and thus, it was confirmed that the imaging apparatus 1 can image an inspection object at a high speed. The beads flowing through the flow channel at the flow rate of 1 m/s, which corresponds to 10,000 beads passing through the photographing position in the imaging apparatus 1 per second. The imaging apparatus succeeded in generating images of beads one by one, as described above. Therefore, it was confirmed that the flow cytometer 21 can generate images with a high throughput of 10,000 images/s.

REFERENCE SIGNS LIST 1 imaging apparatus
2 optical source
3 dispersive fiber
4 dispersion element
5 first diffractive grating 10 photo detector
13 PC
16 microfluidic device
18 inspection object
20 inspection object
21 flow cytometer

The invention claimed is:

1. An imaging apparatus for flow cytometry comprising:
an optical source configured to generate a probe beam comprising an optical pulse;
a dispersive fiber configured to carry out dispersive Fourier transformation on the probe beam so as to map a spectrum of the probe beam in a time domain to form a dispersed beam;
a first diffractive grating configured to spatially map the dispersed beam and irradiate an inspection object with the spatially mapped dispersed beam;
a second diffractive grating configured to convert transmitted light transmitted through the inspection object into an optical pulse mapped in a time domain, the second diffractive grating being disposed on the opposite side of the first diffractive grating with the inspection object interposed therebetween;
a beam detection unit configured to detect the transmitted light converted into the optical pulse; and
an image generation unit configured to generate an image of the inspection object in accordance with an intensity of the transmitted light converted into the optical pulse.

2. The imaging apparatus for flow cytometry according to claim 1, wherein
the dispersive fiber is configured to carry out dispersive Fourier transformation on the probe beam so as to map the spectrum of the probe beam in a time domain to form the dispersed beam from equal to or longer than 5 ns to shorter than a pulse period of the probe beam, and wherein
the imaging apparatus is configured such that the dispersed beam from equal to or longer than 5 ns to shorter than the pulse period of the probe beam strikes on the first diffractive grating, subsequently the first diffractive grating diffracts the dispersed beam to spatially map, and then the inspection object is irradiated with the spatially mapped dispersed beam.

3. The imaging apparatus for flow cytometry according to claim 1, wherein
the dispersive fiber includes an optical fiber, and
the optical fiber has a core diameter of 3 to 4 μm.

4. A flow cytometer comprising:
the imaging apparatus for flow cytometry according to claim 1; and
a microfluidic device including a flow channel through which an inspection object can flow together with a fluid, wherein
the imaging apparatus generates an image of the inspection object flowing though the flow channel.

5. The flow cytometer according to claim 4, wherein
the image generation unit is configured to generate a 2D image of the inspection object by continuously generating 1D images of the inspection object flowing through the flow channel and combining the generated 1D images.

6. An imaging method for flow cytometry comprising:
generating a probe beam which is an optical pulse;
carrying out dispersive Fourier transformation on the probe beam so as to map a spectrum of the probe beam in a time domain to form a dispersed beam;
spatially mapping the dispersed beam by a first diffractive grating, and irradiating an inspection object with the spatially mapped dispersed beam;
converting transmitted light transmitted through the inspection object into an optical pulse mapped in a time domain by a second diffractive grating, the second diffractive grating being disposed on the opposite side of the first diffractive grating with the inspection object interposed therebetween;
detecting the transmitted light converted into the optical pulse; and
generating an image of the inspection object in accordance with an intensity of the transmitted light converted into the optical pulse.

7. An imaging method for flow cytometry comprising:
generating a probe beam which is an optical pulse;
carrying out dispersive Fourier transformation on the probe beam so as to map a spectrum of the probe beam in a time domain from equal to or longer than 5 ns to shorter than the pulse period of the probe beam to form a dispersed beam;
spatially mapping the dispersed beam by a first diffractive grating;
irradiating an inspection object with the spatially mapped dispersed beam;
converting transmitted light transmitted through the inspection object into an optical pulse mapped in a time domain by a second diffractive grating, the second diffractive grating being disposed on the opposite side of the first diffractive grating with the inspection object interposed therebetween;
detecting the transmitted light converted into the optical pulse; and
generating an image of the inspection object in accordance with an intensity of the transmitted light converted into the optical pulse.

* * * * *